United States Patent [19]

Sinnett

[11] Patent Number: 4,878,487
[45] Date of Patent: Nov. 7, 1989

[54] ILLUMINATED TISSUE MANIPULATOR FOR OPHTHALMIC SURGERY

[75] Inventor: Kevin B. Sinnett, Mukwonago, Wis.

[73] Assignee: Trek Medical Products, Inc., Oak Creek, Wis.

[21] Appl. No.: 199,109

[22] Filed: May 26, 1988

[51] Int. Cl.[4] .............................................. A61B 1/06
[52] U.S. Cl. ........................................ 128/20; 128/6; 128/23
[58] Field of Search ............................... 128/20, 23, 6

[56] References Cited

U.S. PATENT DOCUMENTS 2,186,143 1/1940 Neugass ................................ 128/20
4,607,622 8/1986 Fritch et al. ............................ 128/6

Primary Examiner—William H. Grieb
Attorney, Agent, or Firm—Michael, Best & Friedrich

[57] ABSTRACT

The illuminated tissue manipulator includes a handpiece and an elongated rigid probe including a tubular body having an outside dimension suitable for insertion through an opening in a patient's eye and terminating in a forward edge extending around a substantial portion of the outer periphery generally perpendicular to the longitudinal axis of the probe body. The probe body has an integral, narrow tissue manipulating tool which extends longitudinally and outwardly beyond such forward edge. An elongated fiber optic light-conducting member extends through the handpiece and the probe body. One end of the light-conducting member extends in a plane generally perpendicular to the longitudinal axis of the probe body and is disposed adjacent the forward edge of the probe body and the other end is remote from the handpiece and includes an optical connector which is connected to a light source. The tool portion has a rounded tip and can be straight, or the forward end portion including the tip bent inwardly at an acute angle or into a generally J-shape.

7 Claims, 1 Drawing Sheet

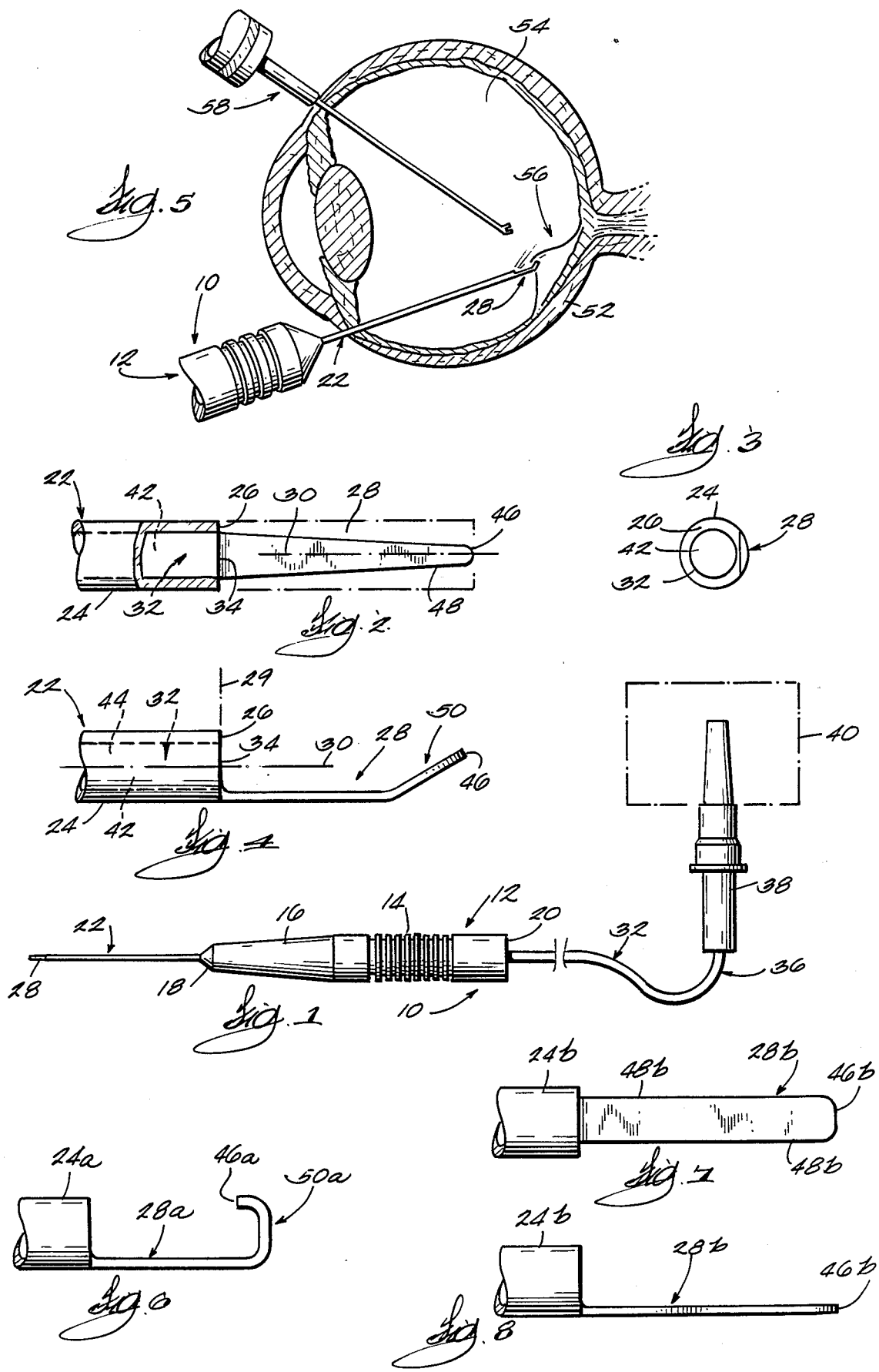

ILLUMINATED TISSUE MANIPULATOR FOR OPHTHALMIC SURGERY

BACKGROUND OF THE INVENTION

This invention relates to medical instruments and, more particularly, to illuminated tissue manipulators for ophthalmic surgery and the like.

During ophthalmic surgery, such as surgery to repair a detached retina, it is important to have a light inside the patient's eye so that the posterior portion of the eye is illuminated well enough to permit the surgeon to readily observe the area of repair. Vitreous membrane pulling the retina forward because of traction must be cut and stripped to relieve the tension so that the retina can lay flat.

With the most widely used prior instruments, the surgeon has to hold a light probe inserted through an incision in the eye in one hand and strip and cut membrane with an instrument inserted through another incision in the eye and held in the other hand. In some cases, separate instruments are used for stripping and manipulating membrane and for cutting the membrane. Consequently, one must be removed and replaced with the other during the surgery procedure. In extreme cases, it may even be necessary to use a light probe, a tissue stripping or manipulating instrument and a cutting instrument inserted through three separate incisions in the eye.

Attempts have been made to either modify or add components to ophthalmic light probes so that they can also serve as a tissue manipulator. Such attempts generally have met with limited success, primarily because the light beam at the tip of the light probe is diffused in an undesirable manner or the additional parts make the device too costly and/or add bulkiness which requires a larger than normal incision in the patient's eye for admission.

SUMMARY OF THE INVENTION

An object of the invention is to provide an illuminated instrument which can be used to manipulate tissue during ophthalmic surgery and the like.

Another object of the invention is to provide such an instrument which is capable of directing a substantially undiffused light beam toward a work area.

A further object of the invention is to provide such an instrument including a one piece probe.

A still further object of the invention is to provide such an instrument which can be formed from existing light pipes.

A yet further object of the invention is to provide such an instrument which can be discarded after use.

Other objects, aspects and advantages of the invention will become apparent to those skilled in the art upon reviewing the following detailed description, the drawing and the appended claims.

The invention provides an illuminated instrument for manipulating vitreous tissue and the like including a handpiece, an elongated rigid probe extending from one end of the handpiece and including a tubular body having an outside dimension suitable for insertion through an opening in a patient's eye and terminating in a forward edge extending around a substantial portion of the outer periphery and having an integral, narrow tissue manipulating tool extending longitudinally and outwardly beyond the forward edge of the probe body. An elongated fiber optic light-conducting member, which extends through the handpiece and probe body, has one end disposed adjacent the forward edge of the probe body and a remote end including means for receiving light from a light source for intraocular illumination whereby a beam of light from the source is directed outwardly from the forward end of the light-conducting member. The forward end of the light-conducting member and the probe body extend in planes generally perpendicular to the longitudinal axis of the probe body. The tool preferably has a rounded tip.

In one embodiment, the outer portion of the tool including the tip is bent inwardly and at an acute angle to the longitudinal axis of the probe body.

In another embodiment, the outer portion of the tool including the tip is bent inwardly in a generally J-shape.

The tool can be formed from existing light pipes by grinding away a forward end portions of the probe body and the light-conducting member.

BRIEF DESCRIPTION OF THE DRAWINGS

FIG. 1 is a fragmentary, side elevational view of an illuminated instrument of the invention.

FIG. 2 is an enlarged top plan view of the tool portion of the instrument illustrated in FIG. 1, shown during the forming process.

FIG. 3 is an end view of the tool portion illustrated in FIG. 2.

FIG. 4 is a side elevational view of the tool portion illustratd in FIG. 2 after the outer portion including the tip has been bent at an acute angle.

FIG. 5 is a cross sectional view of a human patient's eye illustrating the use of the instrument of FIGS. 1–4 in conjunction with intraocular scissors to cut vitreous membrane during retinal repair surgery.

FIG. 6 is a view similar to FIG. 4 illustrating an alternate arrangement for the tool portion.

FIG. 7 and 8 are views similar to FIGS. 2 and 4, respectively, illustrating another alternate arrangement of the tool portion.

DESCRIPTION OF THE PREFERRED EMBODIMENTS

While the instrument of the invention can be used for a variety of differnet applications requiring illumination at a work site and means for manipulating tissue or the like, it is particularly adaptable for use in retinal repair surgery and will be described in connection with that application.

Referring to FIG. 1, an illuminated tool 10 embodying the invention includes an elongated handpiece 12 having a grooved gripping portion 14, a tapered forward portion 16, a first or forward end 18 and a second or rear end 20. The instrument also includes an elongated, rigid probe 22 which is mounted in the forward end 18 of the handpiece 12 and has a tubular body 24.

The probe body 24 (FIGS. 2–4) has an outside dimension suitable for admission through an incision in a human patient's eye into the vitreous cavity, a forward edge 26 extending around a substantial portion of, but not the entire, outer periphery of the probe body 24 and a narrow tissue manipulating tool 28 which is an integral part of the probe body 24 and extends longitudinally and outwardly beyond the forward edge 26 of the probe body 24 The forward edge 26 of the probe body 24 preferably extends in a plane 29 generally perpendicular to the longitudinal axis 30 of the probe body 24.

The instrument 10 also includes a flexible fiber optic light-conducting member 32 which extends through the handpiece 12 and the probe body 24, has a first or forward end 34 disposed adjacent the forward edge 26 of the probe body 24 and has a second or remote end 36 remote from handpiece 12. The forward end 34 of the light-conducting member 32 preferably extends in a plane generally perpendicular to the longitudinal axis 30 of the probe body 24, most preferably generally coincidental with the plane 29 of the forward edge 26 of the probe body 24. Connected to the remote end 36 of the light-conducting member 32 is a conventional optic connector 38 which is adapted to connect the light-conducting member 32 to a suitable light source 40 for intraocular illumination (illustrated schematically).

The light-conducting member 32 is a fiber optic assembly of conventional design used in ophthalmic light probes or pipes and includes a core 42 of a resinous material, such as an acrylic material, and the portion external to the probe 22 is protected by a fluorocarbon polymer, such as Teflon.

The probe 22 preferably resembles a needle for a hypodermic syringe and can be 20 gauge stainless steel with an outside diameter of 0.040 inch or less.

In the embodiment illustrated in FIG. 4 the tissue manipulating tool 28 has a rounded forward end or tip 46 and opposed sides 48 which converge from the forward edge 26 of the probe body 24 toward the tip 46. The forward portion 50 of the tool 28 including the tip 46 is bent inwardly toward and at an acute angle (e.g., 30°-50°) to the longitudinal axis 30 of the probe body 24.

Referring to FIG. 5 the instrument 10 can be inserted through an incision in a patient's eyeball 52 into the vitreous cavity 54. The light beam transmitted through the forward end 34 of the light-conducting member 32 illuminates the posterior portion of the eye in the area of a detached retina 56. The tool portion 28 of the instrument 10 can be used to manipulate tissue and/or membrane which must be stripped and/or cut to permit the retina 56 to lay flat for reattachment. As illustrated in FIG. 5, intraocular scissors 58 inserted through another incision in the patient's eyeball 52 can be used in conjunction with the instrument 10 to cut membrane. The illumination from the light-conducting member 32 permits the surgeon to readily observe the membrane while it is being stripped and/or manipulated with the tool 28 and cut with the scissors 58.

The tool 28 can be formed before the probe 22 is asssembled with the handpiece 12 and the light-connecting member 32 is installed. In a preferred technique, the tool 28 is formed in the probe of existing disposable ophthalmic light pipes including a stainless steel probe, a plastic (e.g., nylon) optic connector and a plastic (e.g. nylon) handpiece so that the instrument can be discarded after use. This can be accomplished by cooling the probe of existing ophthalmic light pipes in a cryogenic medium, and grinding away a forward end portion of both the probe and the light-conducting member to a depth completely through the light-conducting member to leave a segment of the probe of about 0.150 inch long and about 0.065 inch thick as shown in FIGS. 2 and 4. The reduced temperature prevents the plastic core 42 of the light-conducting member 32 from melting during the grinding operation. It also permits the forward end 34 of the core 42 to be ground to a relatively smooth, flat surface which is generally perpendicular to the longitudinal axis 30 of the probe body 2 so that there is very little, if any, diffusion of the light beam transmitted therethrough and the light beam is transmitted generally straight ahead. In FIG. 2 the forward end portion of the probe of an existing light pipe prior to grinding is illustrated by dashed lines. It should be readily apparent that, in order for the light to be so directed, the body is made from a substantially opaque material, such as stainless steel. The segment of the probe body remaining after the initial grinding operation is illustrated in FIG. 3.

The sides 48 of the segment are tapered to form a tip 46 which is on the order of about 60% of the full width of the segment and the tip 46 is rounded by subsequent grinding operations. The forward portion 50 of the tool 28 including the tip 46 is thereafter bent inwardly to an acute angle to the longitudinal axis 30 of the probel body 24.

In the embodiment illustrated in FIG. 6, the tapered forward portion 50a of the tool 28a including the rounded tip 46a is bent inwardly into a hook-like or generally J-shaped after the above-described grinding operations. In the embodiment illustrated in FIGS. 7 and 8, the sides 48b of the tool 28b are not tapered, the tip 6b is rounded and the tool 28b extends in a substantially straight line from the probe body 24b.

From the foregoing description, one skilled in the art can easily ascertain the essential characteristics of the invention and, without departing from the spirit and scope thereof, make various changes and modifications to adapt it to various usages.

What is clamed is:

1. An illuminated instrument for manipulating vitreous tissue and the like comprising
   a handpiece having first and second ends;
   an elongated, rigid probe made from a substantially opaque material, extending from said first end of said handpice and including a tubular body having an outside dimension suitable for insertion through an opening in a patient's eye into the vitreous cavity thereof and terminating in a forward edge extending around a substantial portion of the outer periphery of said body and in a plane generally perpendicular to the longitudinal axis of said body, said body including an integral, narrow tissue manipulating tool extending longitudinally and outwardly beyond said forward edge;
   an elongated fiber optic light-conducting member extending through said handpiece and said body, having a first end disposed adjacent said body forwrad edge and extending in a plane generally perpendicular to the longitudinal axis of said body and having a second end remote from said second end of said hand piece;and
   means connected to second end of said light-conducting member for receiving light from a light source for intraocular illumination whereby a beam of light from said source is directed outwardly through said forward end of said light-conducting member.

2. An instrument according to claim 1 wherein the forward end of said tool terminates in a rounded tip.

3. An instrument according to claim 2 wherein said tool has opposed sides which converge in a direction from said body forward edge toward said tip.

4. An instrument according to claim 3 wherein a forward end portion of said tool including said tip is bent inwardly toward and at an acute angle to the longitudinal axis of said body.

5. An instrument according to claim 3 wherein a forward end portion of said tool including said tip is bent inwardly in a generally J-shape.

6. An instrument according to claim 1 wherein said planes of said body forward edge and said first end of said light-conducting member are generally coincidental.

7. An instrument according to claim 1 wherein said body and said first end of said light-conducting member initially extend beyond said body forward edge and said tool. is formed by grinding away a portion of the forward end portion of said body and grinding through a forward end portion of said light-conducting member.

* * * * *

UNITED STATES PATENT AND TRADEMARK OFFICE
CERTIFICATE OF CORRECTION

PATENT NO. : 4,878,487
DATED : November 7, 1989
INVENTOR(S) : Kevin B. Sinnett

It is certified that error appears in the above-identified patent and that said Letters Patent is hereby corrected as shown below:

Column 4, lines 49 & 50, the word "for-wrad" should read ---forward---.

Column 4, line 54, after the word "to" insert ---said---.

Column 6, line 3, after the word "tool" delete ---.---.

Signed and Sealed this

Twenty-seventh Day of November, 1990

Attest:

HARRY F. MANBECK, JR.

*Attesting Officer*     *Commissioner of Patents and Trademarks*